(12) United States Patent
Narayanan (10) Patent No.: US 6,609,910 B2
(45) Date of Patent: Aug. 26, 2003

(54) TIP FOR DENTAL FLOSSING DEVICE (75) Inventor: Ravikumar S. Narayanan, Fort Collins, CO (US)

(73) Assignee: Water Pik, Inc., Newport Beach, CA (US)

( * ) Notice: Subject to any disclaimer, the term of this patent is extended or adjusted under 35 U.S.C. 154(b) by 0 days.

(21) Appl. No.: 09/746,079

(22) Filed: Dec. 20, 2000

(65) Prior Publication Data

US 2001/0035193 A1 Nov. 1, 2001

Related U.S. Application Data (63) Continuation-in-part of application No. 09/444,043, filed on Nov. 19, 1999, now abandoned.
(60) Provisional application No. 60/171,824, filed on Dec. 21, 1999.

(51) Int. Cl.[7] .................................................. A61C 3/03
(52) U.S. Cl. ....................................... 433/118; 132/322
(58) Field of Search ................................. 433/118, 119, 433/121, 123, 141, 143, 216, 165, 166; 132/322, 321, 329; 601/139, 141

(56) References Cited

U.S. PATENT DOCUMENTS

| 1,355,037 | A |   | 10/1920 | Dziuk |   |
|---|---|---|---|---|---|
| 2,016,597 | A |   | 10/1935 | Drake |   |
| 2,931,371 | A |   | 4/1960 | Petitta |   |
| 3,552,022 | A |   | 1/1971 | Axelsson |   |
| 3,559,292 | A |   | 2/1971 | Weissman |   |
| 3,563,233 | A |   | 2/1971 | Bodine |   |
| 3,590,814 | A |   | 7/1971 | Bennett et al. | ............. 601/139 |
| 3,660,902 | A |   | 5/1972 | Axelsson |   |
| 3,672,378 | A |   | 6/1972 | Silverman |   |
| 3,809,977 | A |   | 5/1974 | Balamuth et al. |   |
| 3,967,617 | A |   | 7/1976 | Krolik |   |
| 4,048,723 | A |   | 9/1977 | Thorup |   |
| 4,205,664 | A |   | 6/1980 | Baccialon |   |
| RE30,536 | E |   | 3/1981 | Perdreaux, Jr. |   |
| 4,271,854 | A | * | 6/1981 | Bengtsson | ................... 132/329 |
| 4,289,486 | A |   | 9/1981 | Sargeant | ..................... 433/118 |
| 4,319,377 | A |   | 3/1982 | Tarrson et al. | ................ 15/111 |
| 4,319,595 | A |   | 3/1982 | Ulrich |   |
| 4,326,547 | A |   | 4/1982 | Verplank |   |

(List continued on next page.)

FOREIGN PATENT DOCUMENTS

| DE | 42 23 196 A1 | 1/1994 |
| DE | 42 26 659 A1 | 2/1994 |
| DE | 43 09 078 A1 | 9/1994 |
| DE | 297 15 234 U1 | 12/1997 |
| EP | 0 354 352 | 2/1990 |
| EP | 0 661 025 B1 | 7/1995 |
| FR | 429447 | 9/1911 |
| WO | WO 94/04093 | 3/1994 |
| WO | WO 95/02375 | 1/1995 |

Primary Examiner—Kevin Shaver
Assistant Examiner—Melba Bumgarner
(74) Attorney, Agent, or Firm—Dorsey & Whitney LLP (57) ABSTRACT A flossing tip for a power dental flossing device. The tip is elongated and includes a base portion, a central portion having a generally rectangular cross-section, and an enlarged end portion including a disk shape. The tip is compressible. The base portion supports the tip when the tip is coupled to the dental flossing device. The central portion couples the base portion to the end portion. The end portion is inserted between a pair of adjacent teeth of a user, and helps guide and orient the tip between the adjacent teeth. When in use, the rectangular cross-section of the tip provides multiple points of contact against a tooth for cleaning, and also helps maintain the tip in proper orientation with respect to the teeth. The enlarged end portion assists in positioning the tip, provides additional cleaning edges, and helps prevent trauma to the gums.

12 Claims, 11 Drawing Sheets

U.S. PATENT DOCUMENTS

| | | | |
|---|---|---|---|
| 4,326,548 A | 4/1982 | Wagner | |
| 4,347,839 A | 9/1982 | Youngclaus, Jr. | |
| 4,397,327 A | 8/1983 | Hadary | |
| 4,505,678 A | 3/1985 | Andersson | |
| 4,522,595 A * | 6/1985 | Selvidge | 433/142 |
| 4,576,190 A | 3/1986 | Youssef | |
| 4,577,649 A | 3/1986 | Shimenkov | |
| 4,608,019 A | 8/1986 | Kumabe et al. | |
| 4,617,718 A | 10/1986 | Andersson | |
| 4,634,376 A | 1/1987 | Mossle et al. | |
| 4,791,940 A | 12/1988 | Hirschfeld et al. | |
| 4,820,153 A | 4/1989 | Romhild et al. | |
| 4,820,154 A | 4/1989 | Romhild et al. | |
| 4,879,781 A | 11/1989 | Desimone | 15/110 |
| 4,913,133 A | 4/1990 | Tichy | |
| 4,913,176 A * | 4/1990 | DeNiro | 132/329 |
| 4,922,936 A | 5/1990 | Buzzi et al. | 132/321 |
| 4,995,403 A | 2/1991 | Beckman et al. | 128/776 |
| 5,000,684 A | 3/1991 | Odrich | 433/125 |
| 5,002,487 A | 3/1991 | Tichy | 433/122 |
| 5,050,625 A | 9/1991 | Siekmann | 132/323 |
| 5,069,621 A | 12/1991 | Paradis | 433/147 |
| 5,071,348 A | 12/1991 | Woog | 433/118 |
| 5,100,321 A | 3/1992 | Coss et al. | 433/118 |
| 5,123,841 A | 6/1992 | Millner | 433/125 |
| 5,133,661 A | 7/1992 | Euvrard | 433/120 |
| 5,169,313 A | 12/1992 | Kline | 433/143 |
| 5,170,809 A | 12/1992 | Imai et al. | 132/322 |
| 5,224,500 A | 7/1993 | Stella | 132/322 |
| 5,236,358 A | 8/1993 | Sieffert | 433/119 |
| 5,393,229 A | 2/1995 | Ram | 433/118 |
| 5,573,020 A | 11/1996 | Robinson | 132/322 |
| 5,588,452 A | 12/1996 | Peck | 132/321 |
| 5,700,146 A | 12/1997 | Kucar | 433/82 |
| 5,709,233 A | 1/1998 | Boland et al. | 132/322 |
| 5,718,667 A | 2/1998 | Sugimoto et al. | 60/139 |
| 5,738,575 A | 4/1998 | Bock | 433/216 |
| 5,775,346 A | 7/1998 | Szyszkowski | |
| 5,787,908 A | 8/1998 | Robinson | 132/322 |
| 5,827,064 A | 10/1998 | Bock | 433/216 |
| 5,855,216 A | 1/1999 | Robinson | 132/322 |
| 5,944,033 A | 8/1999 | Robinson | 132/322 |

* cited by examiner

TIP FOR DENTAL FLOSSING DEVICE

RELATED APPLICATIONS AND PRIORITY

This application is a continuation-in-part of application Ser. No. 09/444,043, filed on Nov. 19, 1999, now abandoned, by Narayanan. This application also claims priority from co-pending provisional application Ser. No. 60/171,824, filed on Dec. 21, 1999, by Lang et al. (includes Narayanan), and design patent Ser. No. 29/115,986, filed on Dec. 21, 1999, now U.S. Pat. No. D437,976, by Narayanan et al.

FIELD OF THE INVENTION

This invention relates to a dental tip attachable to a power dental flossing device for cleaning between adjacent teeth and between the teeth and gum of a user.

BACKGROUND OF THE INVENTION

Power dental flossing devices are motorized devices used to clean or floss the area between a user's teeth and between the teeth and surrounding gums. A power dental flossing device is provided with a removable tip for placement in the interdental or interproximal space between adjacent teeth and in the pockets between the teeth and gums. When the power dental flossing device is activated, the tip, if properly oriented, contacts and rubs against portions of the sides of adjacent teeth and between the gum and adjacent teeth, and helps to dislodge particles and remove plaque forming in those locations.

Conventional tips have a circular or square cross-section, and typically provide only one contact point along the side of a tooth being cleaned. One problem, which can occur with a power dental flossing device, is that ineffective cleaning may result if the tip is mis-oriented when inserted into the interproximal space between teeth. In particular, when the tip is mis-oriented, the area of the surface to be cleaned, contacted and accessed by the tip, is reduced thus reducing the efficiency of the cleaning. Further, a mis-oriented tip is more likely to break during use, or may become stuck between teeth.

What is needed is a tip for a power dental flossing device which provides improved cleaning and whose shape assists a user with properly orienting and inserting the tip between teeth.

SUMMARY OF THE INVENTION

In light of the above, and according to a broad aspect of the invention, disclosed herein is a flossing tip for a power dental flossing device. The flossing tip is elongated and includes a base portion, a central portion, and an end portion. The base portion supports the tip when the tip is connected to the dental flossing device. The central portion has a substantially rectangular cross-section, and couples the base portion to the end portion. The end portion is inserted between a pair of adjacent teeth of a user, and helps guide the tip between the adjacent teeth. When in use, the substantially rectangular cross-section of the tip provides multiple points of contact against a tooth for cleaning, and also helps maintain the tip in proper orientation with respect to the teeth, thus providing more effective cleaning.

According to another broad aspect of the invention, the central portion has a top and a bottom surface, and a pair of sides, wherein the height of the sides is larger than the width of the top and bottom surfaces. The sides contact and engage the sides of the teeth, and in this manner, the tip is less likely to be rotated and mis-oriented once the tip is inserted between the teeth. In one example of the present invention, the sides of the central portion of the tip are curved, preferably inwardly.

The cross-sectional area of the tip along the central portion decreases along the length of the tip from the base portion to the end portion. The central portion has a top surface having a first width at the base portion, and a second smaller width proximate the end portion. Likewise, the height of the sides of the central portion decreases from the base portion to the end portion. In order to reduce the possibility of damage to the gums such as by poking, the edges of at least the central portion are rounded and the end portion of the tip is curved.

In another embodiment of the present invention, the tip has at least one strip of reinforcing material embedded with the central portion, for improved durability of the tip while maintaining the general flexibility of the tip.

In a further embodiment of the present invention, the tip has a disk-shaped end portion. The disc-shaped end portion helps guide the tip between the teeth in the proper orientation and further provide additional cleaning edges. It also acts as a relatively blunt leading edge to reduce aggravation of sensitive gums.

According to another broad aspect of the invention, a method of flossing teeth with a dental flossing device is disclosed. The method includes the step of providing a tip with a substantially rectangular cross-section adapted to be inserted between a pair of teeth of a user, the tip adapted to be attached to the dental flossing device. The user then inserts the tip between the pair of teeth, and activates the power dental flossing device, thereby moving the tip at least vertically upwardly and downwardly along at least a portion of one side of the pair of teeth, or between a tooth and the surround gum, for cleaning.

The foregoing and other features, utilities and advantages of the invention will be apparent from the following more particular description of a preferred embodiment of the invention as illustrated in the accompanying drawings and claims.

DETAILED DESCRIPTION OF A PREFERRED EMBODIMENT

Figure 1:
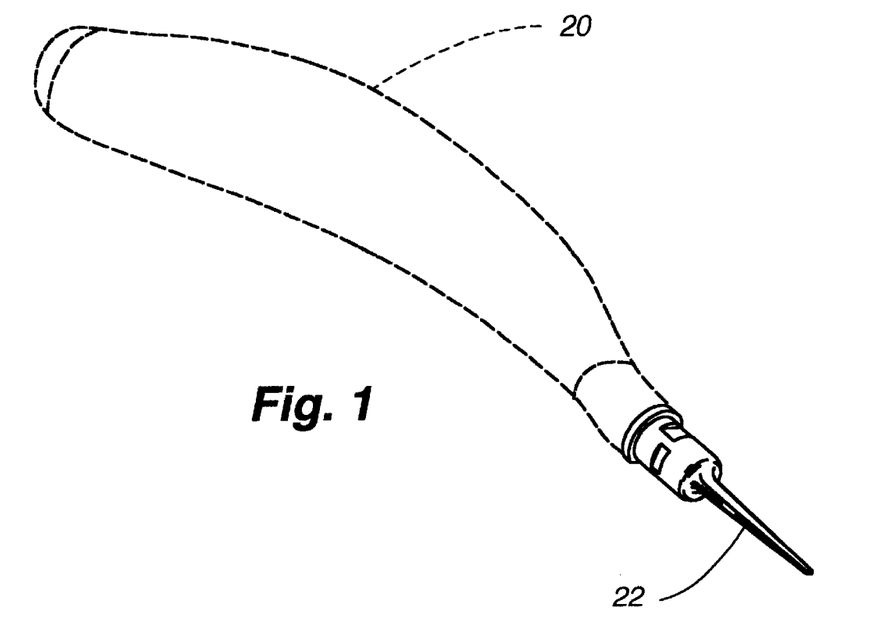
FIG. 1 illustrates an isometric view of a power dental flossing device having a tip, in accordance with one embodiment of the present invention, attached thereto.

Referring to FIG. 1, a power dental flossing device 20 incorporating a flossing tip 22 of the present invention is disclosed. The flossing tip is generally elongated and has a generally rectangular cross-section of decreasing size along the length of the tip, terminating at an end, which is inserted within the space between a pair of teeth. The tip 22 is resilient, flexible, compressible, and generally capable of withstanding forces imposed during the cleaning action. In one embodiment of the present invention, the tip 22 is made from materials such as Isoplast, Polybutylene Teriphthalate (PBT), acetal, ZYTEL™ (preferably type 101L) by DUPONT, nylon such as type 6/6, glass-filled material, or the like.

Figure 9:
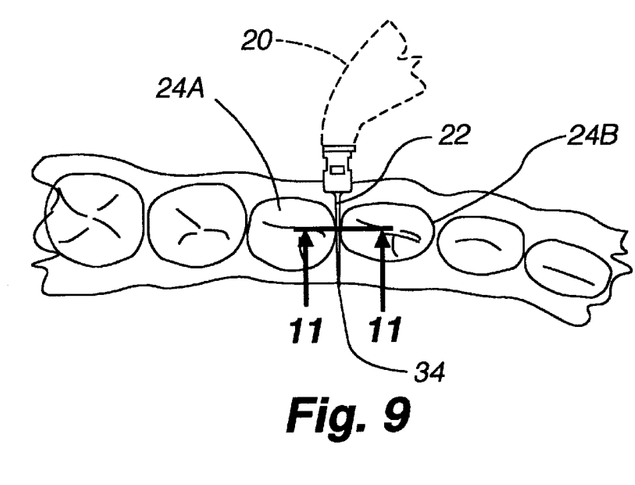
FIG. 9 illustrates a power dental flossing device with a tip in accordance with one embodiment of the present invention, inserted between a pair of adjacent teeth during use.
Figure 11:
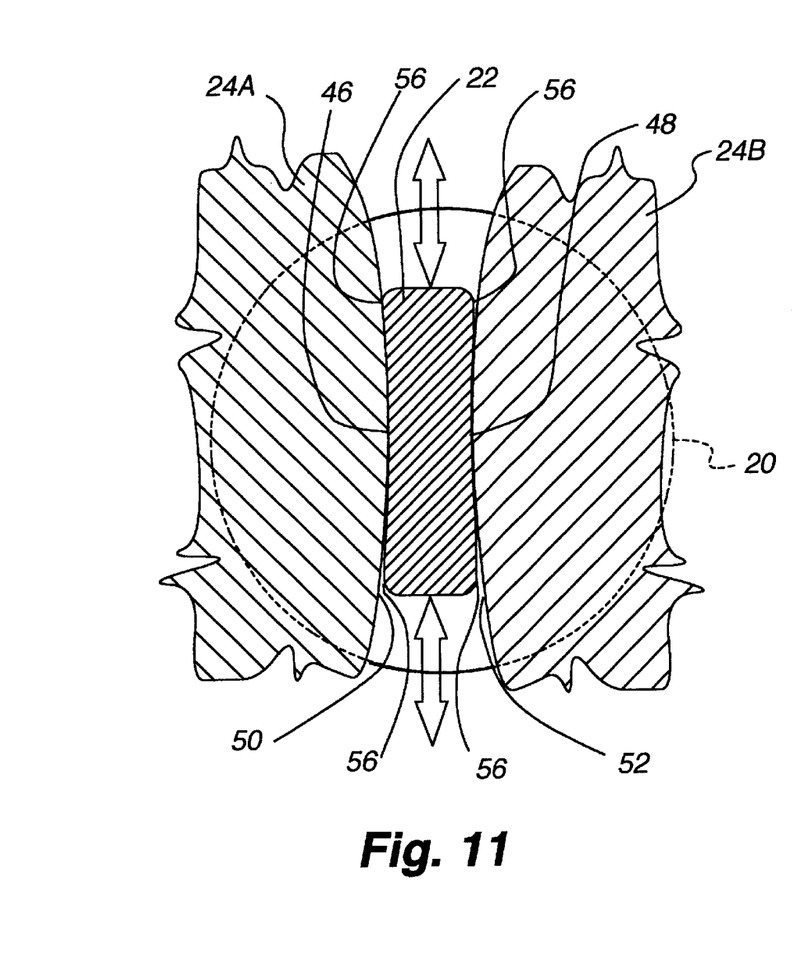
FIG. 11 is an exploded sectional view taken along section lines 11—11 of FIG. 9, and illustrates a tip in accordance with one embodiment of the present invention, inserted between a pair of adjacent teeth as the tip moves vertically upwardly and downwardly during use.

The tip 22 is adapted for use with a power dental flossing device 20, as shown in FIGS. 1 and 9, where the tip 22 is inserted by a user between adjacent teeth 24A, 24B for flossing. In one example of the present invention, the power dental flossing device 20 is a motorized device which is adapted to move the tip 22 in a linear direction, such as in a vertical direction upwardly and downwardly, during use as shown in FIG. 11. As will be described below, due to the unique shape of the tip 22 of the present invention, the tip provides multiple points of contact with the teeth being cleaned and maintains the proper orientation of the tip between teeth, which generally improves the effectiveness of the cleaning action of the power dental flossing device.

Figure 2:
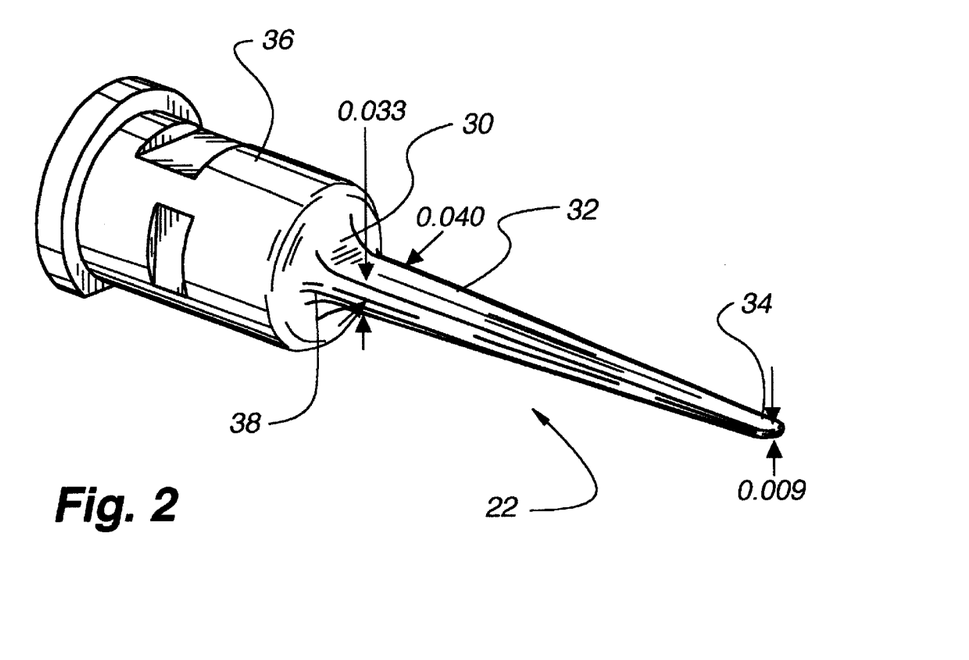
FIG. 2 illustrates an isometric view of a tip for a power dental flossing device, in accordance with one embodiment of the present invention.
Figure 4:
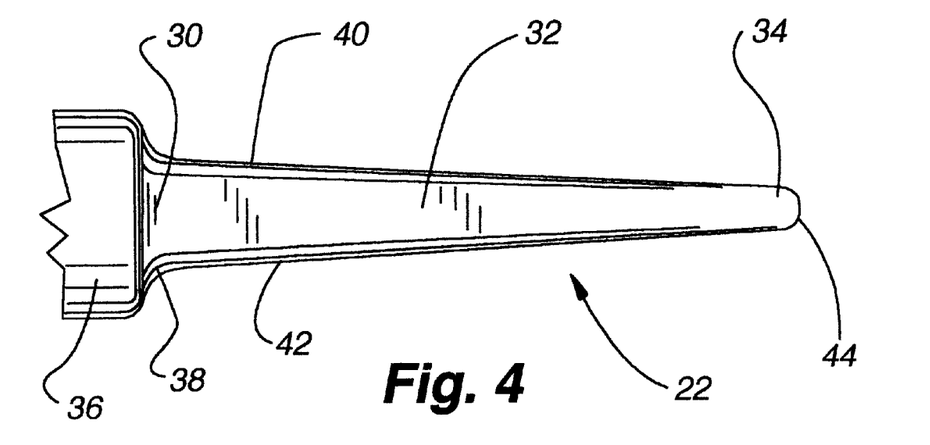
FIG. 4 illustrates a side view of the tip of FIG. 2, in accordance with one embodiment of the present invention.

Referring now to FIGS. 2 and 4, in accordance with the present invention, the flossing tip 22 is an elongated member and includes a base portion 30, a central portion 32, and an end portion 34. The base portion 30 is attached to a connector portion 36, which is adapted to removably attach to an end of the power dental flossing device 20. In one example, the base portion 30 includes a fillet 38 having a generally triangular cross-section. The fillet 38 extends around the perimeter of the base portion and attaches the base portion 30 to the connector portion 36. The base portion 30 and the fillet 38 assist to distribute the stresses incurred along the tip 22 during use, and provide a solid foundation for supporting and connecting the tip 22 to the power dental flossing device 20 through the connector portion 36. In one example, the base portion 30 shown in FIGS. 2 and 4 has a length of approximately 0.026 inches from the connector portion to the top of the fillet 38.

Figure 3:
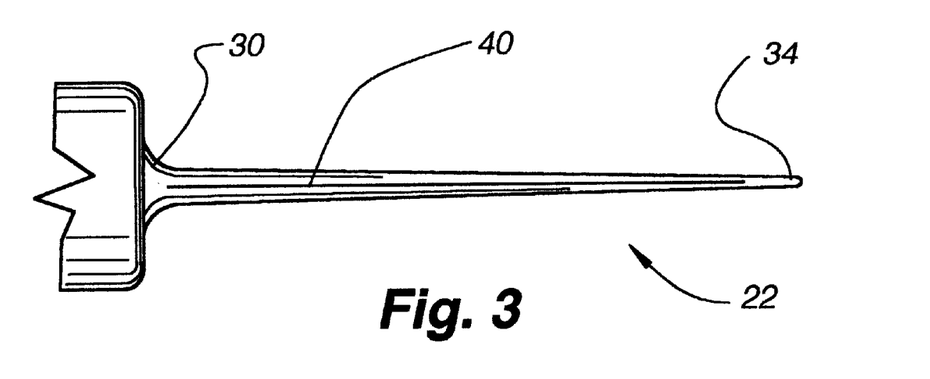
FIG. 3 illustrates a top view of the tip of FIG. 2, in accordance with one embodiment of the present invention.
Figure 7:
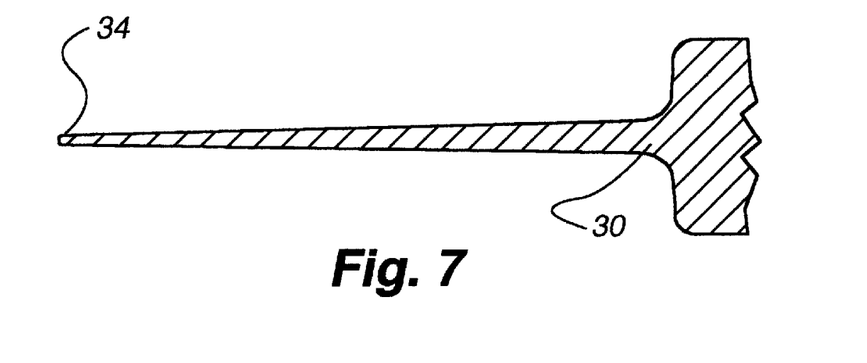
FIG. 7 illustrates a sectional view of the tip taken along section lines 7—7 of FIG. 6, in accordance with one embodiment of the present invention.

The central portion 32, which extends between the base portion 30 to the end portion 34 of the tip 22, has a top and bottom surface 40, 42 which define a width and height dimension. Referring to FIGS. 3 and 7, the width of the top surface 40 decreases along the length of the central portion 32 from the base to the end portion 34. In one example, the width is approximately 0.027 inches proximate the base portion 30, and the width is approximately 0.006 inches proximate the end portion 34. Preferably, the bottom surface 42 of the central portion 32 is substantially identical, in dimensions and shape, to the top surface 40; although the top and bottom surfaces may have different widths at any point along the tip thereby forming an angular cross-sectional profile, if desired. The length of the central portion 32 is approximately 0.51 inches in one example.

Alternatively, the tapering of the top and bottom surfaces 40, 42 can begin after a certain distance (for example, approximately 0.180 inches) along the length of the central portion 32, thereby increasing the mass of the tip proximate the base, which imparts greater strength to the entire tip.

Figure 6:
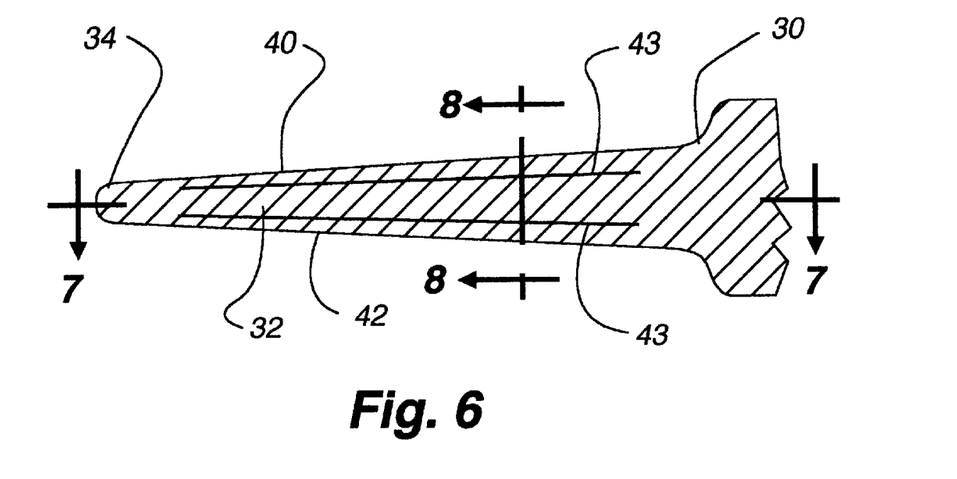
FIG. 6 illustrates a sectional view of the tip, in accordance with one embodiment of the present invention.

Referring to FIGS. 4 and 6, the top and bottom surfaces 40, 42 of the central portion 32 also define a height dimension that decreases along its length, being a maximum at the base 30 and a minimum at the end portion 34. Preferably, the central portion 32 has a height of approximately 0.077 inches proximate the base portion 30, and has a height of approximately 0.031 inches proximate the end portion 34.

Since the width of the top and bottom surfaces 40, 42 decreases along the length of the tip 22 from the base portion 30 to the end portion 34, and the height of the tip likewise decreases, these decreasing dimensions form a flossing tip which is easily slidably inserted between adjacent teeth, while also providing a flossing tip which maintains its orientation once inserted between the adjacent teeth. When the user has finished flossing between a pair of adjacent teeth, the tip is also easily removed from between the teeth due to these decreasing dimensions.

Further, in one example, the top and bottom surfaces 40, 42 of the central portion 32 can be embedded with thin strips 43 of reinforcing material such as metal, spring steel or the like, so as to increase the strength and durability of the tip while maintaining the resilient, flexible nature of the tip. One or more strips 43 are preferably encased in the material of the tip to protect the user's teeth and gums against contact with the strip. However, certain types of materials can be used for the strip 43 to avoid this effect.

Alternatively, a core made of stainless steel, or other reinforcing material, can be embedded within the central portion of the tip to increase the strength and durability of the tip while maintaining the resilient, flexible nature of the tip. The core has a shape generally similar to the central portion, but with smaller dimensions. In one example, the core is approximately 0.475 inches in length. Proximate the base end of the core, the core has a height of approximately 0.025 to 0.030 inches, and a thickness of approximately 0.010 inches. Proximate the end portion, the core has a height of approximately 0.008 to 0.010 inches, and a thickness of approximately 0.003 inches.

Figure 5:
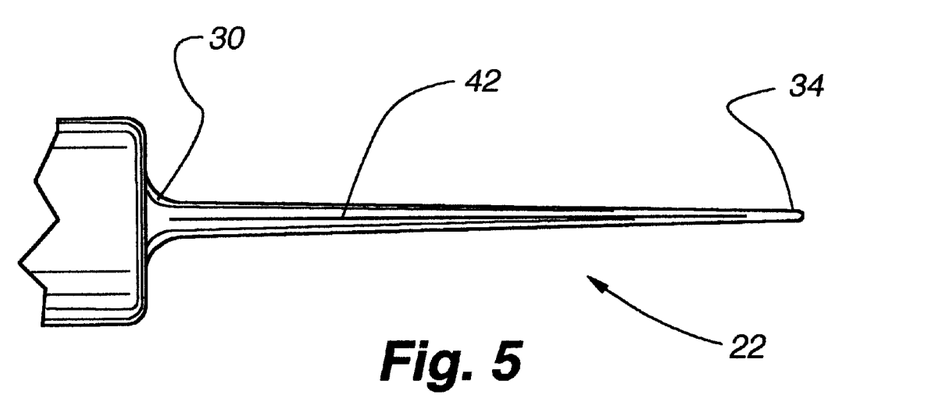
FIG. 5 illustrates a bottom view of the tip of FIG. 2, in accordance with one embodiment of the present invention.

The central portion 32 transitions to the end portion 34 of the tip 22. Referring to FIGS. 4 and 5, the end portion 34 is generally flat along its sides and is rounded, which assists the user in guiding the tip properly within the interproximal space between adjacent teeth, and reduces trauma to the gums. Referring to FIG. 4, the end portion 34 has a rounded or curved end 44, in one example, having a radius of curvature of approximately 0.02 inches. As mentioned above, the end portion has a width along its top and bottom surfaces of approximately 0.006 inches, and a height of approximately 0.031 inches, preferably. The end portion could have other shapes also, but the curved shape is desired for easily guiding the tip between teeth and for being comfortable, and reduces trauma to the gums.

Figure 10:
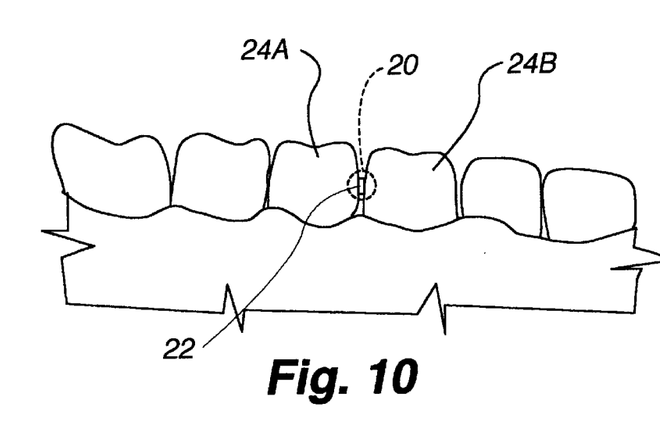
FIG. 10 illustrates a power dental flossing device with a tip in accordance with one embodiment of the present invention, inserted between a pair of adjacent teeth during use.

Referring to FIGS. 9–11, as the tip 22 is slid between adjacent teeth, the end portion 34 of the tip 22 assists in dislodging food particles therein, and the sides 46, 48 of the tip 22 press against the sides 50, 52 of the adjacent teeth 24A, 24B which aligns the tip between the teeth as the tip is slid between the teeth. The distance, which the tip 22 needs to be inserted between the teeth for alignment to occur, will depend on the particular distance between the teeth 24A, 24B and the space between the teeth and gums of a user. Since the gap between teeth is generally a vertical slot, once a sufficient amount of the central portion 32 of the tip 22 has been inserted between the teeth, the tip is aligned therein. Since the tip 22 is made of resilient flexible material, the tip 22 of the present invention generally maintains its alignment between the teeth, as can be seen in FIGS. 9 and 11, even if the handle of the power dental flossing device 20 is slightly moved or slightly rotated (which may mis-align a conventional tip thereby generally decreasing the effectiveness of cleaning).

Figure 8:
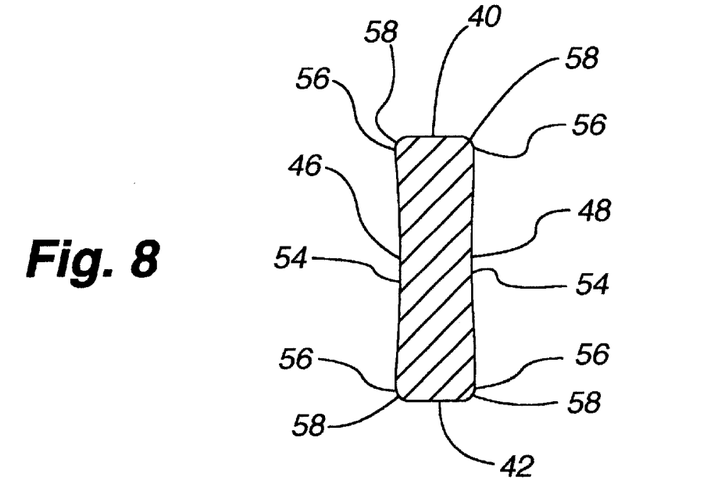
FIG. 8 illustrates a sectional view of the tip taken along section lines 8—8 of FIG. 6, in accordance with one embodiment of the present invention.

As shown in FIGS. 8 and 11, the cross-sectional geometry of the tip 22, at a section taken about the central portion 32, generally forms a rectangle in one example, defined by the top and bottom surfaces 40, 42 and the sides 46, 48 of the central portion 32. Preferably, the sides 46, 48 of the central portion 32 are longer than the width of the top and bottom surfaces 40, 42, which permits at least one side of the tip 22 to engage at least one side of a tooth during use. Preferably, the sides 46, 48 of the tip are curved inwardly towards one another, with a radius of curvature being approximately 0.20 inches in one example. The curve can have a variety of shapes, such as a simple curve or a complex curve, preferably a simple curve.

Referring to FIG. 8, a neck 54 is formed at the point where the tip has its narrowest thickness along the curved sides 46, 48. In one example, the neck 54 is formed along the curved sides 46, 48 at a midpoint between the top and bottom surfaces 40, 42 of the tip 22. Preferably, the neck 54 has a thickness of approximately 0.02335 inches at a point proximate the base portion 30; and a thickness of approximately 0.00587 inches proximate the end portion 34 of the tip. The varying thickness of the neck 54 along the length of the tip assists a user in guiding the tip between adjacent teeth, while providing a tip, which is usable for flossing between teeth having various inter-proximal distances therebetween. The substantially rectangular cross-section also helps impart strength to the entire tip.

The curved sides 46, 48 help to improve the cleaning efficiency by improving the contact area between the sides 46, 48 of the tip 22 and the sides of the teeth. As can be seen in FIGS. 8 and 11, each curved side 46, 48 provides at least two points of contact 56 with a side of each tooth being flossed variously during the flossing process. During flossing, in one example, the tip compresses inwardly from the sides as the tip is moved between teeth, so that the tip can move into and through spaces narrower than the distance between the contact point on the top or bottom edge, respectively. The cross-sectional geometry of the tip shown in FIGS. 8 and 11 is preferably generally rectangular with inwardly curved sides, because such a structure is easily manufactured and provides a strong cross-sectional structure, which is also resiliently compressible. Other shapes, such as I-beam shaped, dog-bone shaped, or oval-shaped, are also feasible for providing indented or inset side walls.

Figure 12:
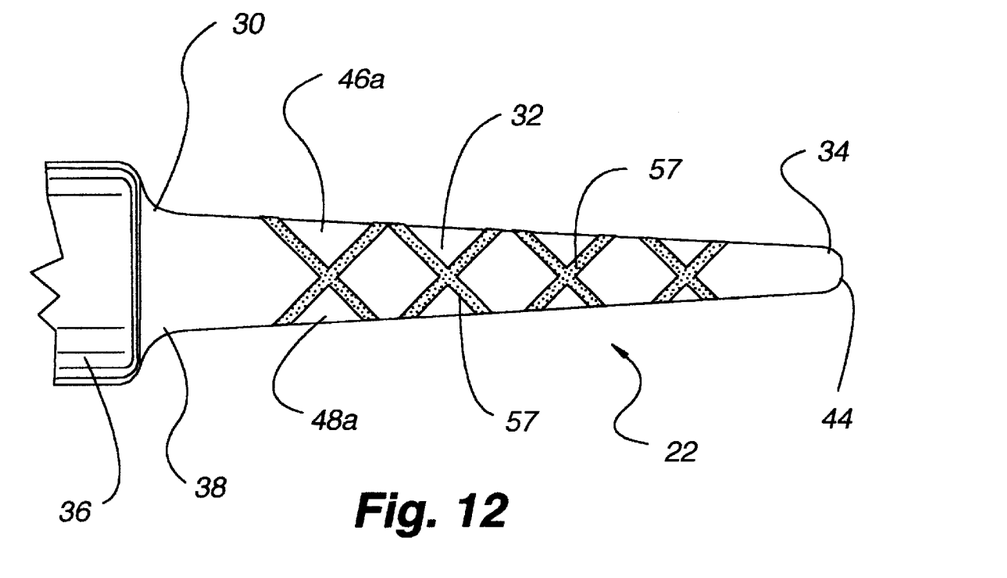
FIG. 12 illustrates a side view of an alternative embodiment of the tip of FIG. 2 of the present invention, where the tip has a surface treatment thereon.

In an alternative embodiment as shown in FIG. 12, sides 46a, 48a have a surface treatment 57, such as a cross-hatching pattern, thereon. The surface treatment 57 generally helps improve the cleaning effectiveness of the tip by providing a plurality of gripping edges along the length of the tip to help break down plaque. In one example, the surface treatment 57 is formed on the sides of the tip by etching or cutting thin grooves or ridges or indentations in the sides 46a, 48a. Alternatively, a set of ribs or protrusions can be formed along the sides 46a, 48a, in a crosshatch or other pattern, to form the surface treatment 57. The protrusions can be made, for example, by etching thin grooves of ridges in the mold cavity of the tip. While a crosshatch surface treatment 57 is shown, other surface treatments using different patterns or different densities of the pattern, may be used to improve the cleaning effectiveness of the tip.

The edges 58 of the tip, as shown in FIGS. 8 and 11, are preferably rounded which help prevent damage or injury to the gums of a user upon incidental contact with the tip 22 during use.

During use and referring to FIGS. 9, 10, and 11, the flossing tip 22 of the present invention, being coupled to a power dental flossing device 20, is inserted by the user between adjacent teeth 24A, 24B and the gum line. The end portion 34 of the tip 22 can dislodge any food particles embedded between the adjacent teeth. As the tip 22 is inserted deeper between the adjacent teeth, the curved sides 46, 48 of the central portion 32 of the tip engage the sides 50, 52 of the teeth. As the power dental flossing device 20 is activated and the tip 22 moves linearly, preferably vertically upwardly and downwardly, the contact points 56 of the tip, along with portions of the curved sides 46, 48 of the tip, rub against the sides 50, 52 of the teeth 24A, 24B to break up plaque and provide a dental cleaning action. The contact points move up and down in the space between the teeth to clean the sidewalls of the teeth. Since the tip is resiliently compressible, the contact points at the top and bottom edges of the tip can compress and extend to fit the differing dimensions of the gap to maintain contact. The user can move the tip to contact and clean different portions of the sides of the teeth, and the tip will generally maintain the proper orientation with respect to the teeth to continue to provide an effective dental cleaning action.

Another embodiment of the present invention includes a flossing tip 22 having an enlarged end portion 70 as illustrated in FIGS. 13–18. With exception of the end portion 70, the flossing tip 22 including an enlarged end portion 70 is substantially similar to the flossing tip 22 illustrated in FIGS. 2–8. However, the enlarged end portion 70 provides enhanced cleaning, guidance, and gum protection in the area of use. The enlarged end portion 70 extends in a relative vertical direction (the same direction as the motion of the tip 22 and the orientation of the interproximal space), and not in the lateral direction. The enlarged end portion 70 tapers to its leading edge 72 to provide access to tight interdental spaces (the wedge effect). The varying flex characteristics along the length of the tip 22 gives the user control over the application force of the tip against the tooth and gum. The length of the tip 22 provides access to the full depth of the interdental space, as measured from the outside of the gum (cheek) to the inside of the gum (tongue side), and also allows access into the spaces between the teeth and surrounding gums.

Figure 13:
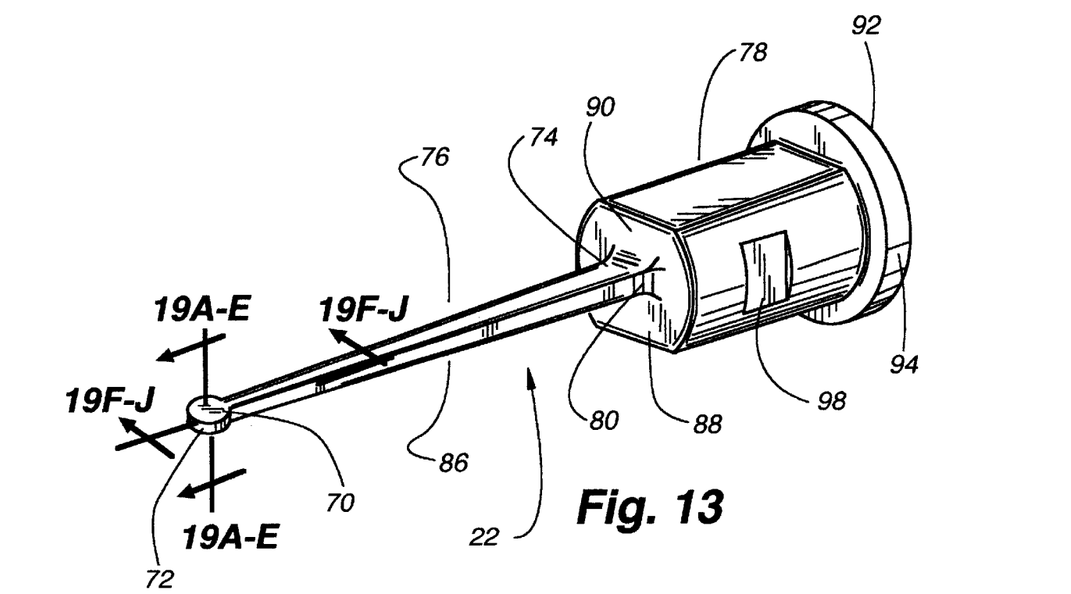
FIG. 13 is a front isometric view of a tip for a power dental flossing device, in accordance with one embodiment of the present invention.
Figure 14:
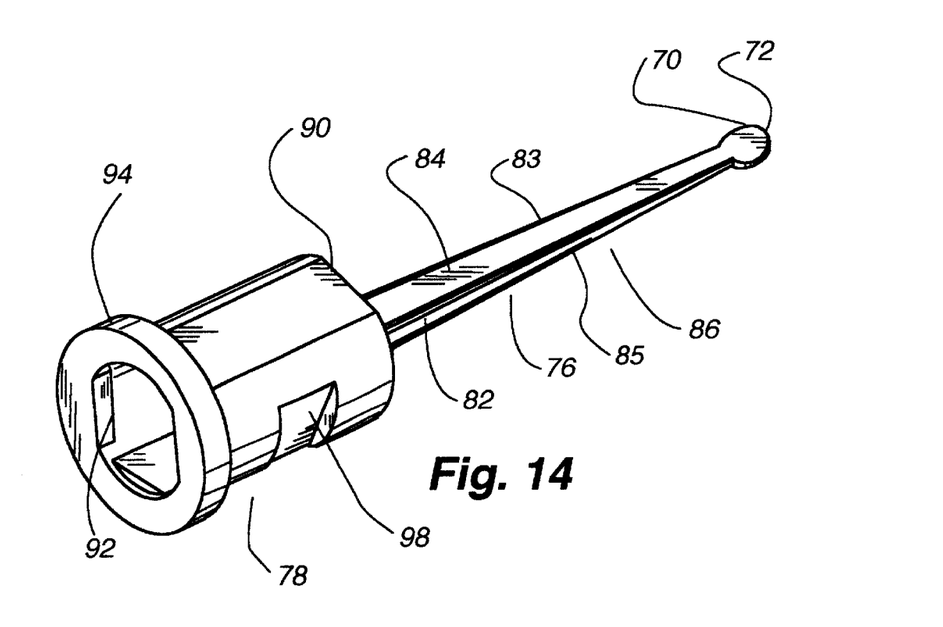
FIG. 14 is a rear isometric view of the tip of FIG. 13, in accordance with one embodiment of the present invention.
Figure 15:
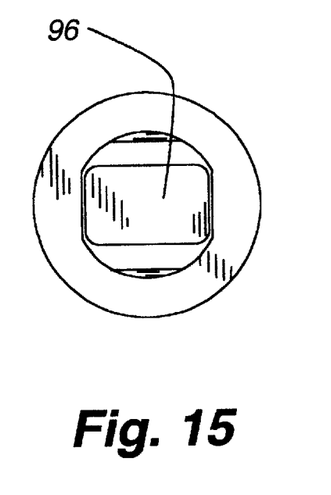
FIG. 15 is a rear view of the tip of FIG. 13, in accordance with one embodiment of the present invention.

Referring to FIGS. 13–14, the flossing tip is generally an elongated member and includes a base portion 74, a central portion 76, and an enlarged end portion 70. The base portion 74 is attached to a connector portion or tip connection structure 78, which is adapted to removably attach to the end of a power dental flossing device.

In the embodiment illustrated in FIG. 13, the base portion 74 includes a fillet 80 having a substantially rectangular cross-section. The fillet 80 extends around the perimeter of the base portion 74 and attaches the base portion 74 to the connector portion 78. The base portion 74 and the fillet 80 assist to distribute the stresses incurred by the flossing tip 22 during use, and provide a solid foundation for supporting and connecting the flossing tip 22 to the power dental flossing device through the connector portion 78.

Figure 16:
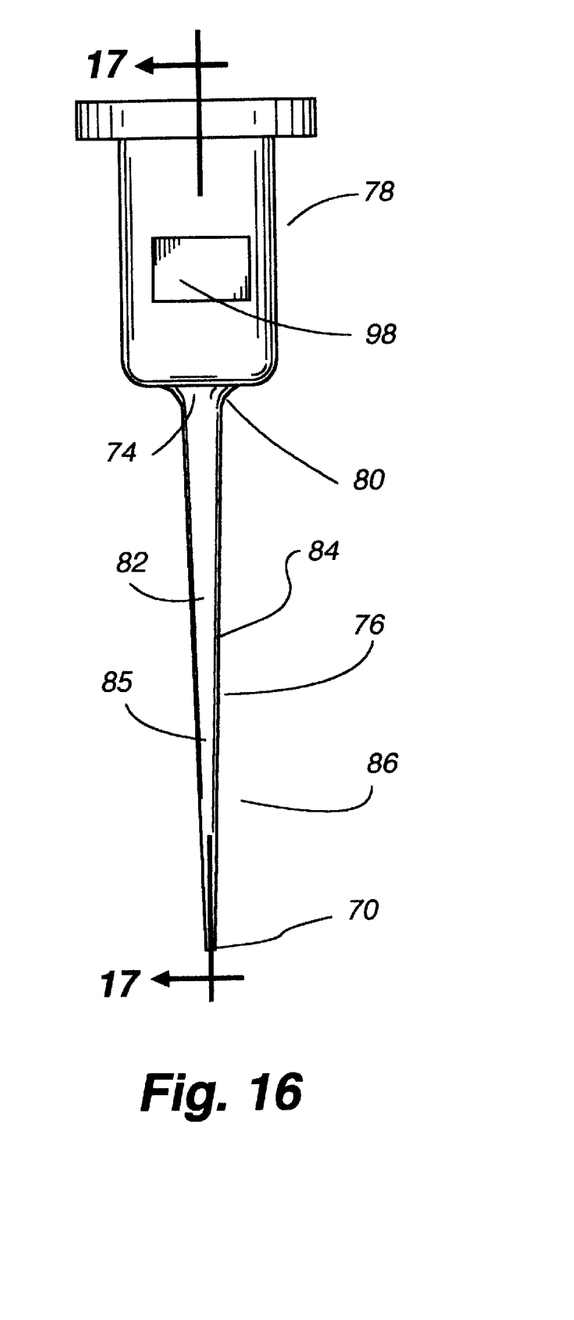
FIG. 16 is a top view of the tip in FIGS. 13–15, in accordance with one embodiment of the present invention.
Figure 17:
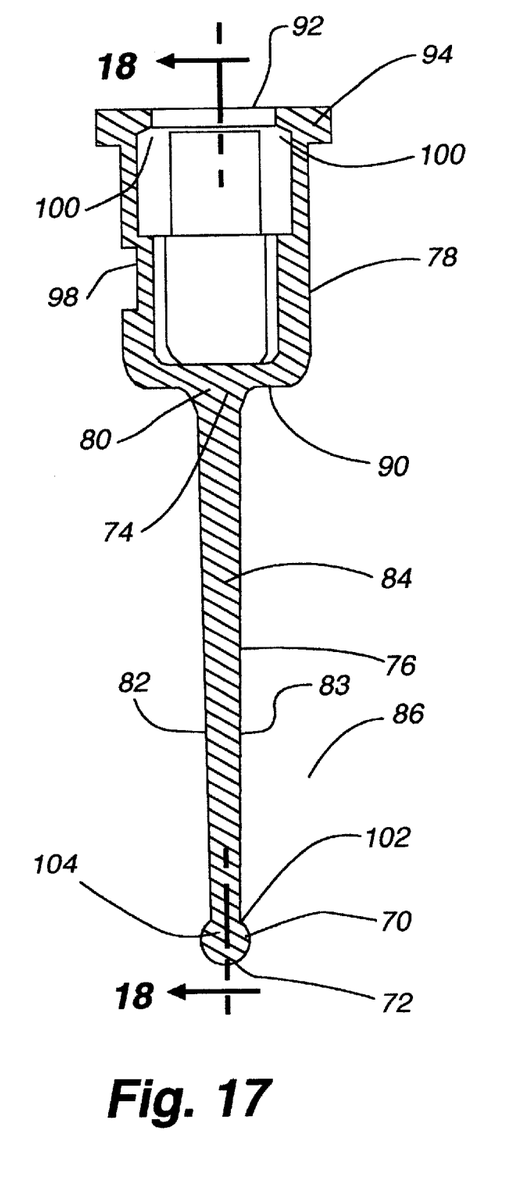
FIG. 17 is a section view of the tip taken along line 17—17 of FIG. 16.
Figure 17A:
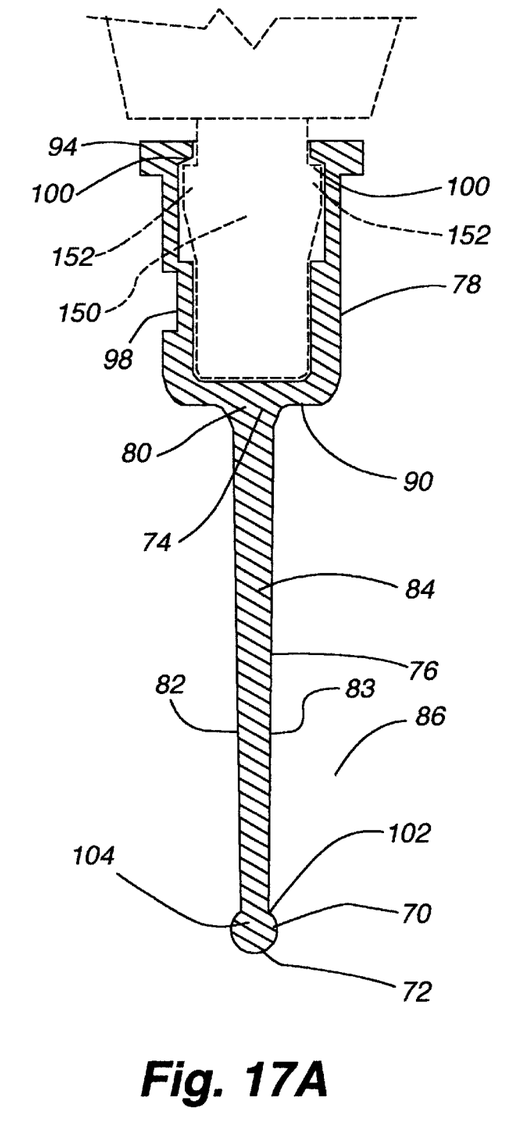
FIG. 17A is the section view of FIG. 17 with a flossing device rocking arm inserted into the tip (in dash).

The central portion 76, which extends between the base portion 74 to the end portion 70 of the flossing tip 22, has top and bottom surfaces 82, 83 which define a width and height dimension. Referring to FIGS. 16 and 17, the width of the top surface 82 decreases along the length of the central portion from the base through the end portion. Preferably, the bottom surface 83 of the central portion 76 is substantially identical, in dimensions and shape, to the top surface 82; although the top 82 and bottom 83 surfaces may have different widths at any point along the tip thereby forming an angular cross-sectional profile, if desired.

Referring to FIGS. 14 and 17, the top and bottom surfaces 82, 83 of the central portion 76 also define a height dimension of sides 84 and 85 that decreases along its length, being a maximum at the base 74 and a minimum at the end portion 70. Preferably, the central portion 76 has a height of approximately 0.077 inches proximate the base portion 74, and has a height of approximately 0.031 inches proximate the end portion 70.

Alternatively, the tapering of the top 82 and bottom 83 surfaces can begin after a certain distance along the length of the central portion, thereby increasing the mass of the tip 22 proximate the base 74, which imparts greater strength to the entire tip 22.

FIGS. 13–18 also illustrate the specific detailed structure of the flossing tip. The flossing tip includes a tip connection structure 78 from which extends the flossing element 86. The flossing element 86 and tip connection structure 78 are made of a plastic. The flossing element 86 extends from the center of the end 88 of the tip connection structure 78 and can be straight, curved, or angular, or a combination of any of these. The flossing element 86 is sized to be received in the interproximal spaces. The flossing element 86 may have a pointed end, a disk-shaped end, or any other shaped end sized to be received in the interproximal spaces. Further details regarding the design of the flossing tip 22 are provided in U.S. patent application Ser. No. 09/636,488, filed Aug. 10, 2000, which is hereby incorporated by reference in its entirety.

The tip connection structure 78 has a cup-like shape forming a cavity with a closed end 90 from which the flossing element 86 extends and an open end 92, which receives the top end portion of a flossing device rocker arm 150. The interior of the tip connection structure 78 cavity forms a tip connection structure for releasably securing the flossing tip 22 to the top end of the flossing device rocker arm 150. Adjacent the closed end, diametrically opposed recesses 100 are formed on the interior wall of the tip connection structure 78. The purpose of the latching recesses 100 will be described in greater detail below. The tip connection structure 78 is typically generally cylindrical, but can be deformed to an oval shape as described below. The open end 92 and cavity of the tip connection structure 78 form a rectangular aperture 96 allowing the tip 22 to be mounted one of two ways on the end of the rocker arm 150. The open end 92 of the tip connection structure 78 extends radially outward to form a rim 94 on the open end 92 of the tip connection structure 78. The exterior of the tip connection structure 78 is generally smooth and includes one production indentation 98 that is not related to the functioning of the flossing tip 22. The flossing tip 22 is removed and stored by utilizing a means to engage the tip connection structure 78 rim 94. Further details regarding the removal and storage of the flossing tips 22 and the design of a tip connection structure are provided in U.S. Provisional Patent Application No. 60/148,915, filed Aug. 13, 1999, and U.S. patent application Ser. No. 09/636,488 filed Aug. 13, 2000, which are hereby incorporated by reference in their entirety.

In operation, the enclosed latching recesses 100 in the tip connection structure 78 engage the latching tabs 152 of the mechanism (the top end portion of the rocker arm) to hold the tip 22 in place. The means to engage and disengage the tip 22 are to compress the sides of the tip connection structure 78 and deform it into essentially an elliptical shape. This would create a major axis of an ellipse, which would be larger than the distance across the latching tabs 152 on the top end portion of the rocker arm 150. There is a gap on either side of the top end portion of the rocker arm 150 when inserted in the tip connection structure 78 to allow the tip connection structure 78 to be squeezed to form an elliptical shape. The tip connection structure 78 can deform to an ovalized or non-circular shape to release the latch tabs 152 from the latch recesses 100.

This detent-style tip connection allows for secure placement of the flossing tip 22 on the top end of the rocker arm 150 yet also allows for convenient removal of the flossing tip 22 from the top end portion of the rocker arm 150. The tip connection structure 78 is slidingly engaged over the top end portion of the rocker arm 150 so that the tip connection structure 78 is gradually increased in size to allow the rocker arm latch tabs 152 to seat in the tip connection structure 78 latching recesses 100. The tip connection structure 78 is sufficiently resilient to rebound to its circular shape and thus hold the tip 22 on the top end portion of the rocker arm 150.

When the flossing tip 22 is positioned on the top end of the rocker arm 150, an audible "click" is heard when the flossing tip 22 is correctly seated thereon. This is a positive feature for assuring the user that the flossing tip 22 is firmly attached to the device.

The one area of concern is that when the flossing tip 22 is ejected from the production mold or the tip sides are compressed to unlatch the tip 22, the sides of the tip at 90 degrees to the detent and latch features may tend to yield and stay in a somewhat elliptical shape. This is not so critical when removed from the device since the tip 22 is designed and intended for one use only. However, if it is distorted when it is ejected from the mold during the manufacturing, its latching ability could be severely affected. The material selected for the tip 22, preferably Dupont Zytel™ 101L, or the like, such as NC010 (nylon 66), is believed to overcome this problem.

At the transition point from central portion 76 to end portion 70, hereinafter referred to as the neck 102, the edge of the end portion 70 extends radially outward to define an enlarged end portion 70. The embodiment illustrated in FIGS. 13, 14 and 17 includes an enlarged end portion 70 having a disk shape. In a particularly preferred embodiment, the overall length of the flossing tip 22 is about 0.5 inches, the cross-sectional height dimension ranges from about 0.040 inches at its tallest point to about 0.018 inches at its shortest point, the cross-sectional width dimension ranges from about 0.033 inches at its widest point to about 0.009 inches at its narrowest point (leading edge 72 of the tip), and the disk diameter is about 0.038 inches.

The width of the top 82 and bottom 83 surfaces decreases along the length of the flossing tip 22 from the base portion 74 through the end portion 70, and the height of the flossing tip 22 then decreases from the base portion 74 to the end portion 70, and the height of the flossing tip 22 increases along the enlarged end portion 70. These dimensions form a flossing tip 22, which is easily slidably inserted between adjacent teeth and between gums and teeth, while also providing a flossing tip 22 which maintains its orientation once inserted between the adjacent teeth. In addition, the enlarged end portion 70 increases the user's comfort by reducing trauma to the gums. Aside from enhancing comfort levels, the enlarged end portion 70 also increases flossing efficiency by providing additional cleaning edges (at least on the top and bottom). When the user has finished flossing between a pair of adjacent teeth, the tip 22 is also easily removed from between the teeth due to this shape.

Figure 18:
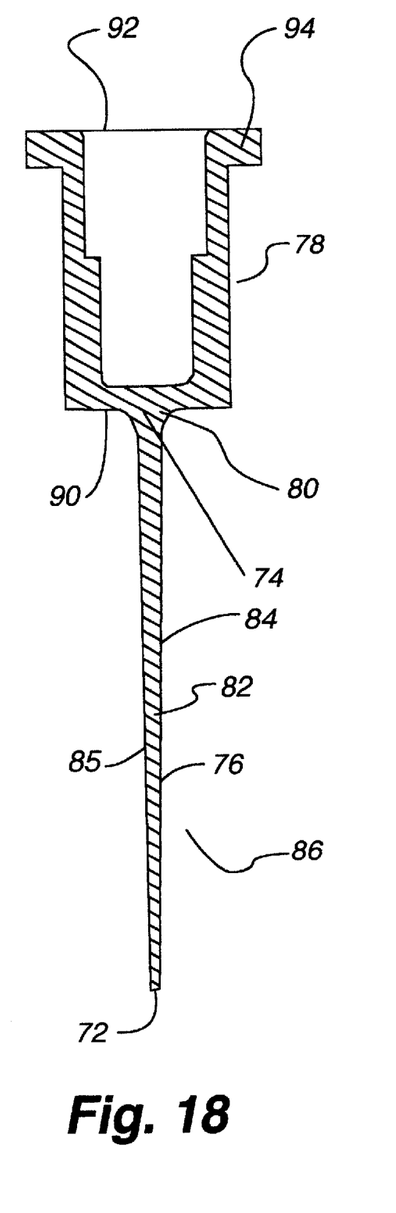
FIG. 18 is a section view of the tip taken along line 18—18 of FIG. 17.
Figure 18A:
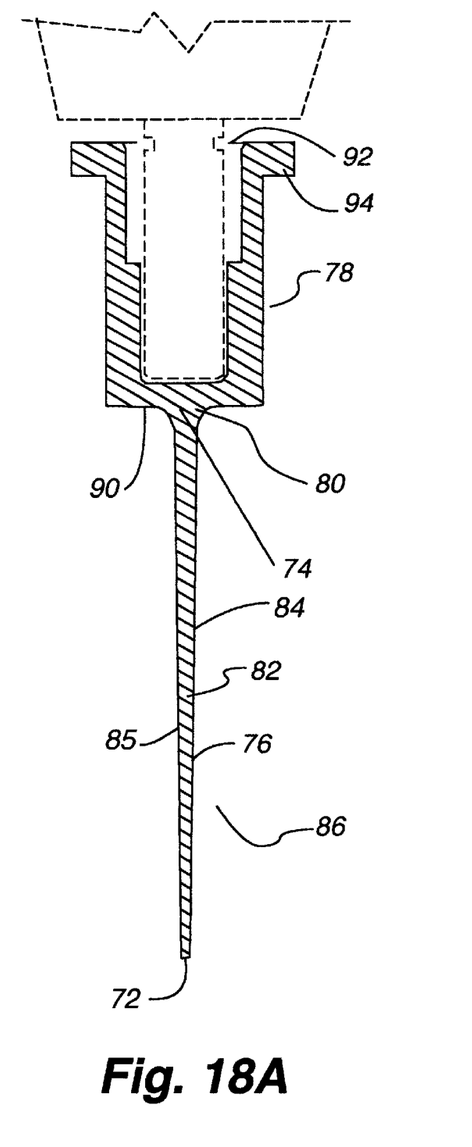
FIG. 18A is the section view of FIG. 18 with a flossing device rocking arm inserted into the tip (in dash).

The central portion 76 transitions to the enlarged end portion 70 of the flossing tip. Referring to FIGS. 13–14 and 17–18, the width of the enlarged end portion 70 decreases from the end of the central portion 76 to the leading edge 72 of the enlarged end portion 70. The leading edge 72 of the enlarged end portion 70 is generally flat, as shown in FIGS. 16 and 18, but can also be smooth and rounded. The height of the enlarged end portion 70 increases radially outward from the end of the central portion to define an enlarged end portion 70 including a rim having a round, disk shape 104. The enlarged end portion 70 assists the user in guiding the tip portion 22 properly within the interproximal space between adjacent teeth, and reduces trauma to the gums. Both the width and height of the disk shape 104 are selected to provide an end portion 70 that easily and comfortably fits between teeth. The end portion 70 could have other shapes also, but the generally flat or tapered disk shape 104 is desired for easily guiding the end portion 70 between teeth, for providing additional cleaning edges, for being comfortable, and for reducing trauma to the gums.

Figure 19A:
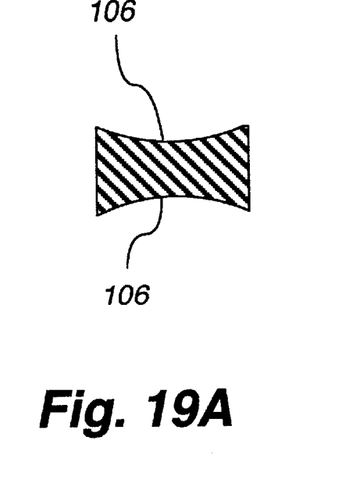
FIGS. 19A–19E are vertical section views taken along line 19AE—19AE of FIG. 13 and FIGS. 19F–19J are longitudinal section views taken along line 19FJ—19FJ of FIG. 13, illustrating alternative embodiments of the present invention.
Figure 19B:
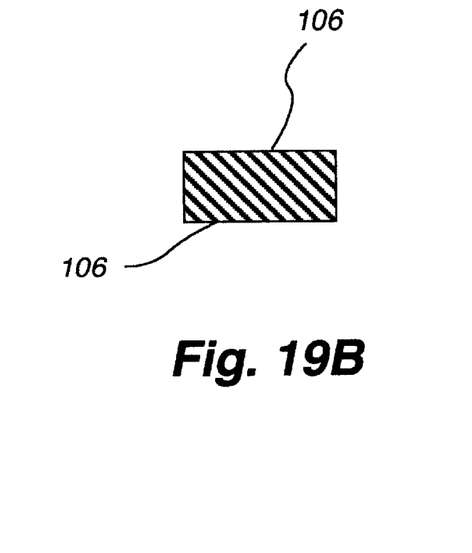
Figure 19C:
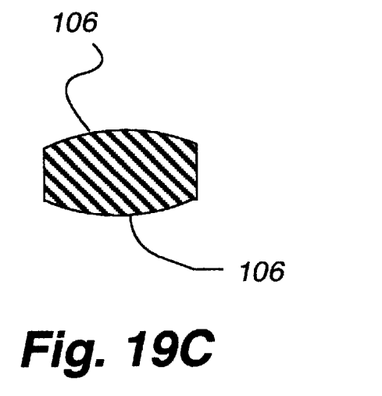
Figure 19D:
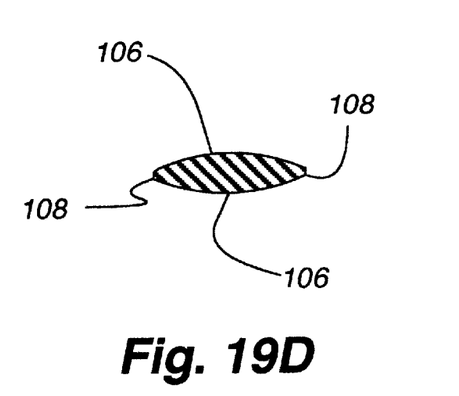
Figure 19E:
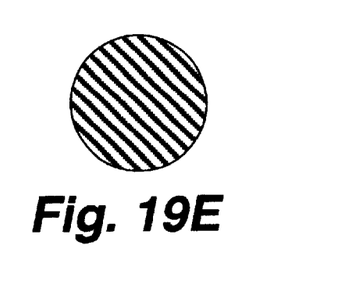
Figure 19F:
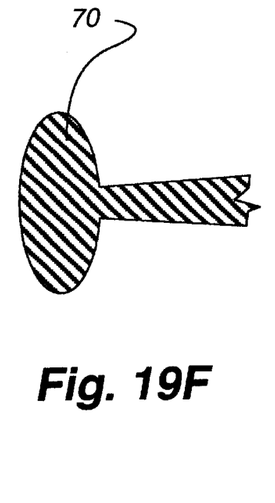
Figure 19G:
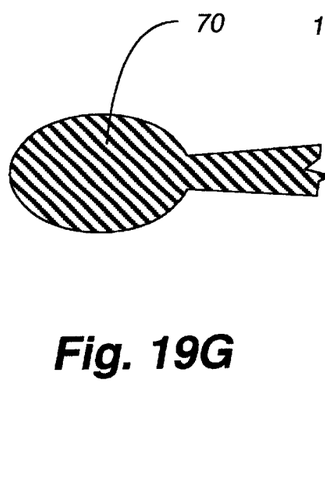
Figure 19H:
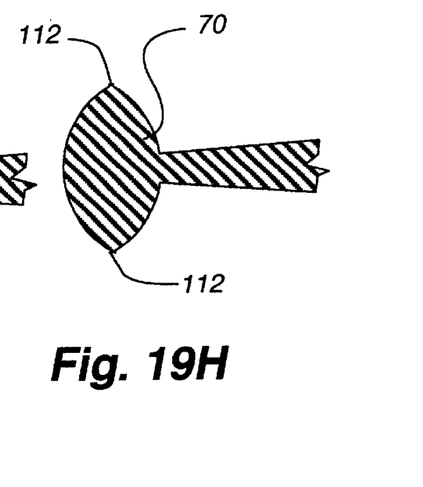
Figure 19I:
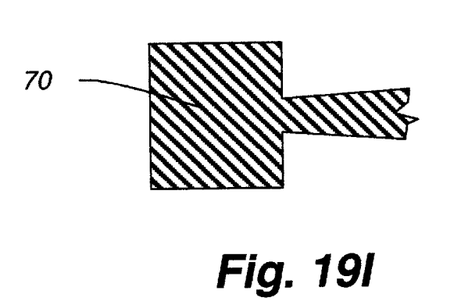
Figure 19J:
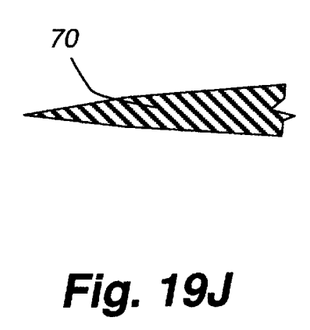

Other embodiments of the flossing tip 22 include flossing tips having enlarged end portions 70 with shapes other than the disk shape 104. In other embodiments, the end portion 70 may include any cross-sectional and/or side view shape providing the dimensions of the end portion are sized to easily and comfortably fit between teeth and between the teeth and gums. FIGS. 19A–19E illustrate vertical section views of alternatively shaped flossing tip end portions taken along the plane transverse to the length of the tip and through the tip end portion. In FIG. 19A, the sidewalls 106 of the tip are concave facing outwardly. In FIG. 19B, the sidewalls 106 of the tip are parallel. In FIG. 19C, the sidewalls 106 of the tip are convex facing outwardly. In FIG. 19D, the sidewalls 106 of the tip convex outwardly, with the top 108 and bottom 110 sides being relatively narrow. In FIG. 19E, the sidewalls of the tip form a continuous circular shape. FIGS. 19F–19J illustrate longitudinal section views of alternatively shaped flossing tip end portions taken along the length of the tip end portion. In FIG. 19F, the end portion 70 is an oblong or oval in a direction transverse to the length of the tip. In FIG. 19G, the end portion 70 is an oblong or oval in a direction in line with the length of the tip. In FIG. 19H, the end portion 70 is an oblong or oval in a direction transverse to the length of the tip, with pointed ends 112. In FIG. 19I, the end portion 70 is square or rectangular. In FIG. 19J, the end portion is pointed. Shapes that both increase the number of cleaning edges and help reduce trauma to the gums are preferred.

Figure 20:
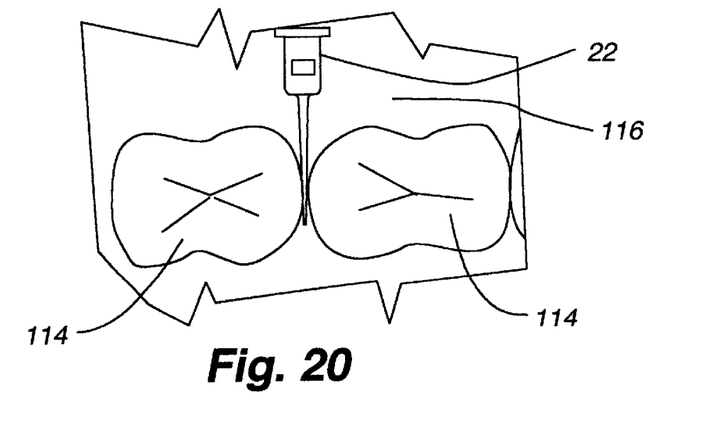
FIG. 20 is the power dental flossing device tip in FIGS. 13–15, in accordance with one embodiment of the present invention, inserted between a pair of adjacent teeth during use.

During use and referring to FIG. 20, the flossing tip 22, including an enlarged end portion 70, of the present invention is inserted by the user between adjacent teeth 114 at the gum line 116, or between the teeth and surrounding gums. Because the tip 22 is properly oriented in a vertical position, the enlarged end portion 70 of the tip is not discernible in FIG. 20. The end portion of the flossing tip can dislodge food particles embedded between the adjacent teeth, or in the space between a tooth and its surrounding gum. The tip preferably stays relatively straight during use, but can bend to allow for some mis-alignment.

While the invention has been particularly shown and described with reference to a preferred embodiment thereof, it will be understood by those skilled in the art that various other changes in the form and details may be made without departing from the spirit and scope of the invention.

What is claimed is:

1. A flossing tip for use with a power dental flossing device, comprising:

a central portion comprising a length, a height, a base end, and a tip end;

a base portion comprising a fillet, said base portion attached to said base end of said central portion;

a disk-shaped end portion extending from said tip end of said central portion, said end portion defining a height greater than said height of said central portion;

a connector portion attached to said base portion, said connector portion adapted to removably attach to said power dental flossing device; and wherein a motion, when powered, of said end portion is in the direction of extension of said end portion from said central portion.

2. The flossing tip of claim 1, wherein said end portion extends in a relative vertical direction from said central portion.

3. The flossing tip of claim 2, wherein said end portion comprises a length sufficient to access a full interdental space extending from the outside of a gum to the inside of a gum.

4. The flossing tip of claim 3, further comprising a fillet having a substantially triangular cross-section taken perpendicularly to a longitudinal axis of the tip, and attached to the base portion.

5. The flossing tip of claim 1, further comprising a fillet having a substantially rectangular cross-section taken perpendicularly to a longitudinal axis of the tip, and attached to the base portion.

6. The flossing tip of claim 5, wherein said fillet extends around a perimeter of said base portion.

7. The flossing tip of claim 6, wherein said fillet attaches said base portion to said connector portion.

8. The flossing tip of claim 7, wherein said fillet distributes along said flossing tip stresses incurred by said flossing tip during use.

9. The flossing tip of claim 1, wherein:

said central portion comprises a top and bottom surface defining a width and said height;

said width of said central portion decreases uniformly along said length of said central portion from said base end to said tip end; and said height of said central portion decreases uniformly along said length of said central portion from said base end to said tip end.

10. The flossing tip of claim 9, wherein:

said height of said central portion at said base end is approximately 0.077 inches; and said height of said central portion at said tip end is approximately 0.031 inches.

11. The flossing tip of claim 9, wherein:

said end portion comprises a top and bottom surface defining a width and a length, said width of said end portion matches said width of said central portion at a point where said end portion extends from said central portion;

said width of said end portion decreases uniformly along said length of said end portion; and said height of said end portion increases from said point where said end portion extends from said central portion.

12. The flossing tip of claim 1, wherein:

said central portion comprises a top and bottom surface defining a width and said height;

said width of said central portion defines a constant width for a distance beyond said base end; and said width of said central portion decreases uniformly along said length of said central portion after said distance to said tip end.

* * * * *

UNITED STATES PATENT AND TRADEMARK OFFICE
CERTIFICATE OF CORRECTION

PATENT NO. : 6,609,910 B2
DATED : August 26, 2003
INVENTOR(S) : Ravikumar S. Narayanan It is certified that error appears in the above-identified patent and that said Letters Patent is hereby corrected as shown below:

<u>Title page,</u>
Item [63], Related U.S. Application Data, after "abandoned" insert -- , and continuation-in-part of design application No. 29/115,986, filed Dec. 21, 1999, now Pat. No. D437,976 --

Signed and Sealed this

Twenty-seventh Day of July, 2004

JON W. DUDAS
*Acting Director of the United States Patent and Trademark Office*